US010995283B2

(12) United States Patent
Bodas et al.

(10) Patent No.: US 10,995,283 B2
(45) Date of Patent: May 4, 2021

(54) PROCESS FOR NPENTANIZING DEBUTANIZED NATURAL GASOLINE FEEDSTOCK TO THERMAL CRACKERS

(71) Applicant: SABIC Global Technologies B.V., Bergen op Zoom (NL)

(72) Inventors: Vijay Dinkar Bodas, Riyadh (SA); Sultan Al-Otaibe, Riyadh (SA); Guillermo Leal, Riyadh (SA); Mohammed Bismillah Ansari, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/497,908

(22) PCT Filed: Mar. 29, 2018

(86) PCT No.: PCT/IB2018/052205
§ 371 (c)(1),
(2) Date: Sep. 26, 2019

(87) PCT Pub. No.: WO2018/185629
PCT Pub. Date: Oct. 11, 2018

(65) Prior Publication Data
US 2020/0032149 A1 Jan. 30, 2020

Related U.S. Application Data

(60) Provisional application No. 62/480,606, filed on Apr. 3, 2017.

(51) Int. Cl.
*C10G 61/06* (2006.01)

(52) U.S. Cl.
CPC ........ *C10G 61/06* (2013.01); *C10G 2300/104* (2013.01)

(58) Field of Classification Search
CPC .......... C07C 9/15; C07C 7/04; C07C 5/2713; C07C 5/2724; C07C 5/2727; C07C 7/13; C07C 9/18; C07C 2521/04; C07C 2521/06; C07C 2523/42; C07C 2527/053; C07C 2531/02; C07C 7/005; C10G 2300/104; C10G 25/08; C10G 35/00; C10G 35/04; C10G 45/58; C10G 53/08; C10G 59/06; C10G 61/06; C10G 67/06; C10G 69/06; C10G 7/00; C10G 9/36
See application file for complete search history.

(56) References Cited

U.S. PATENT DOCUMENTS

| 7,485,768 | B1 | 2/2009 | Rice et al. ................. 585/734 |
| 2014/0107382 | A1 | 4/2014 | Shecterle et al. ............ 585/258 |
| 2015/0315102 | A1 | 11/2015 | Lapinski et al. | |
| 2016/0185688 | A1 | 6/2016 | Lapinski et al. ............. 585/708 |

OTHER PUBLICATIONS

Vermeiren, W., et al. "Impact of Zeolites on the Petroleum and Petrochemical Industry." Topics in Catalysis; 2009 (52), 9, 1131-1161.
International Search Report and Written Opinion for PCT/IB2018/052205 dated Jun. 6, 2018, 9 pages.

*Primary Examiner* — Sharon Pregler
(74) *Attorney, Agent, or Firm* — Norton Rose Fulbright US LLP (57) ABSTRACT

A process for producing natural gasoline. The process includes increasing the n-pentane concentration of debutanized natural gasoline. The process may include a first concentration process that includes distillation and a second concentration process that includes simulated moving bed adsorption.

19 Claims, 5 Drawing Sheets

```
┌─────────────────────────────────────────────────────────────────┐
│  SPLITTING DEBUTANISED NGL FEEDSTOCK INTO A FIRST FEED          │── 400
│           STREAM AND A SECOND FEED STREAM                        │
└─────────────────────────────────────────────────────────────────┘
                                 ↓
┌──────────────────────────────────────────────────────────────────────┐
│  SUBJECT THE FIRST FEED STREAM TO A CONCENTRATING            401     │
│  PROCESS THAT INCLUDES DISTILLING TO PRODUCE A FIRST                 │
│  PRODUCT STREAM THAT INCLUDES PRIMARILY N-PENTANE                    │
│  AND A SECOND PRODUCT STREAM THAT INCLUDES METHANE,                  │
│  ETHANE, PROPANE, ISOBUTANE, AND N-BUTANE                            │
│  ┌────────────────────────────────────────────────────────────┐      │
│  │ DISTILL A COMBINATION OF THE FIRST FEED STREAM AND A       │      │
│  │ RECYCLE STREAM (COMPRISING PRIMARILY ISOPENTANE),          │      │
│  │ IN A DISTILLATION UNIT TO PRODUCE A BOTTOMS STREAM         │── 401-1
│  │ (COMPRISING PRIMARILY N-HEXANE), AN INTERMEDIATE           │      │
│  │ STREAM (COMPRISING PRIMARILY N-PENTANE), AND AN            │      │
│  │ OVERHEAD STREAM (COMPRISING PRIMARILY ISOPENTANE)          │      │
│  └────────────────────────────────────────────────────────────┘      │
│                               ↓                                      │
│  ┌────────────────────────────────────────────────────────────┐      │
│  │ COMBINE THE INTERMEDIATE STREAM AND BOTTOM STREAM TO       │── 401-2
│  │ PRODUCE THE FIRST PRODUCT STREAM                            │      │
│  └────────────────────────────────────────────────────────────┘      │
│                               ↓                                      │
│  ┌────────────────────────────────────────────────────────────┐      │
│  │ ISOMERIZE THE OVERHEAD STREAM IN A REACTOR TO              │── 401-3
│  │ CONVERT AT LEAST SOME OF OVERHEAD STREAM'S                 │      │
│  │ ISOPENTANE TO N-PENTANE                                    │      │
│  └────────────────────────────────────────────────────────────┘      │
│                               ↓                                      │
│  ┌────────────────────────────────────────────────────────────┐      │
│  │ DISTILL EFFLUENT FROM THE REACTOR TO FORM THE RECYCLE      │── 401-4
│  │ STREAM AND THE SECOND PRODUCT STREAM                       │      │
│  └────────────────────────────────────────────────────────────┘      │
└──────────────────────────────────────────────────────────────────────┘
                                 ↓
┌──────────────────────────────────────────────────────────────────────┐
│  SUBJECT THE SECOND FEED STREAM TO A CONCENTRATING           402     │
│  PROCESS THAT INCLUDES SIMULATED MOVING BED ADSORBING                │
│  TO PRODUCE A THIRD PRODUCT STREAM, WHICH INCLUDES                   │
│  PRIMARILY N-PENTANE AND FOURTH PRODUCT STREAM, WHICH                │
│  INCLUDES PRIMARILY ISOPENTANE                                       │
│  ┌────────────────────────────────────────────────────────────┐      │
│  │ FEEDING SECOND FEED STREAM AT A FIRST PORT IN A SERIES     │── 402-1
│  │ OF ADSORBENT COLUMNS                                       │      │
│  └────────────────────────────────────────────────────────────┘      │
│                               ↓                                      │
│  ┌────────────────────────────────────────────────────────────┐      │
│  │ FEEDING ELUENT AT A SECOND PORT IN THE SERIES              │── 402-2
│  │ OF ADSORBENT COLUMNS                                       │      │
│  └────────────────────────────────────────────────────────────┘      │
│                               ↓                                      │
│  ┌────────────────────────────────────────────────────────────┐      │
│  │ REMOVE RAFFINATE FROM A THIRD PORT IN THE SERIES OF        │── 402-3
│  │ ADSORBENT COLUMNS 318 TO 321                                │      │
│  └────────────────────────────────────────────────────────────┘      │
│                               ↓                                      │
│  ┌────────────────────────────────────────────────────────────┐      │
│  │ SIMULATE SWITCHING LOCATION OF FIRST PORT,                 │── 402-4
│  │ SECOND PORT, THIRD PORT, AND FOURTH PORT                   │      │
│  │ REPEATEDLY AMONGST EACH OTHER                              │      │
│  └────────────────────────────────────────────────────────────┘      │
└──────────────────────────────────────────────────────────────────────┘
```

PROCESS FOR NPENTANIZING DEBUTANIZED NATURAL GASOLINE FEEDSTOCK TO THERMAL CRACKERS

CROSS REFERENCE TO RELATED APPLICATIONS

This application is a national phase application under 35 U.S.C. § 371 of International Application No. PCT/IB2018/052205 filed Mar. 29, 2018, which claims priority to U.S. Provisional Patent Application No. 62/480,606 filed Apr. 3, 2017. The entire contents of each of the above-referenced disclosures is specifically incorporated by reference herein without disclaimer.

FIELD OF INVENTION

The present invention generally relates to producing natural gasoline. More specifically, the present invention relates to increasing the concentration of n-pentane in debutanized natural gasoline.

BACKGROUND OF THE INVENTION

Natural gasoline is a petroleum product that has properties similar to commercial gasoline but it has much lower octane than commercial gasoline. The natural gasoline comes from natural gas processing plants and comprises primarily $C_5$ and $C_6$ hydrocarbons and a small percentage of heavier hydrocarbons and butane. Typically, debutanised natural gasoline is supplied to customers as liquid at ambient temperature. Common uses for natural gasoline are as feedstock for refinery isomerization units and feedstock for thermal cracking units. Also, natural gasoline can be used as a blending component of commercial gasoline or used as feedstock for chemical plants. Debutanized natural gasoline is natural gasoline that has undergone a process to remove butane such that the butane concentration is less than 1.0 wt. %. Debutanised natural gasoline is typically obtained from a series of fractionating columns.

Figure 1:
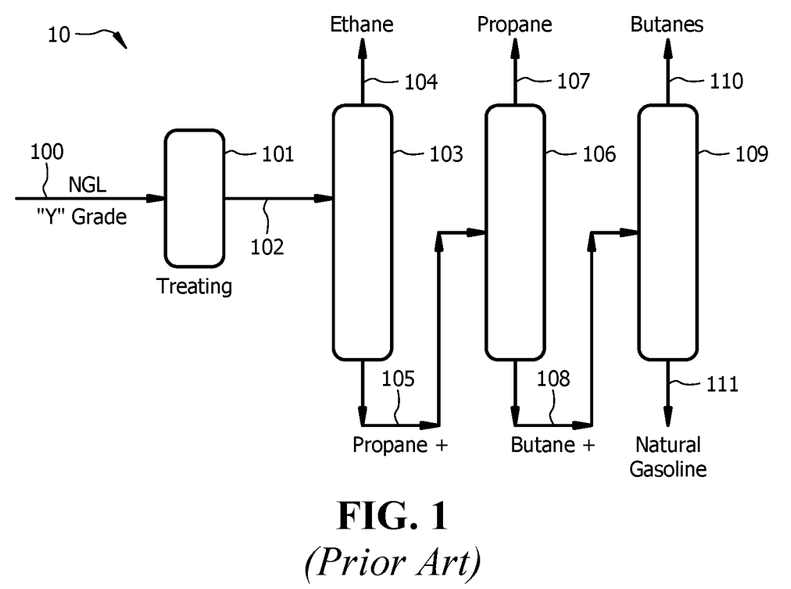
FIG. 1 shows prior art natural gas fractionator system.

FIG. 1 shows prior art natural gas fractionator system 10. Natural gas fractionator system 10 includes natural gasoline (NGL) stream 100 (e.g., Y grade NGL), which feeds into treating unit 101, which pretreats NGL stream 100 to produce stream 102. The pretreatment is typically carried out in an absorption or compression type unit and involves dewatering and demethanising to produce stream 102 (which is dry). Stream 102 flows to fractionating column 103, which separates stream 102 into ethane stream 104 as distillate, and propane+ stream 105 (propane and heavier hydrocarbons) as bottoms. Propane+ stream 105 flows to fractionating column 106, which separates propane+ stream 105 into propane 107 as distillate, and butane+ stream 108 (butane and heavier hydrocarbons) as bottoms. Butane+ stream 108 flows to fractionating column 109, which separates butane+ stream 108 into butane stream 110 as distillate and debutanised natural gasoline 111.

Typically, in debutanized natural gasoline 111, the ratio of linear pentanes/branched pentanes is about 1.28. It is well known that branched hydrocarbon feedstock (e.g., branched pentane) does not crack as well as linear hydrocarbon feedstock.

BRIEF SUMMARY OF THE INVENTION

A method has been discovered that increases the ratio of linear pentanes/branched pentanes in debutanized natural gasoline. By increasing this ratio, the utilization efficiency of debutanized natural gasoline as feedstock to thermal cracking units can be improved.

Embodiments of the invention include a method of increasing n-pentane concentration in debutanized natural gasoline. The method may include splitting a stream that comprises primarily n-pentane and isopentane collectively into a first feed stream comprising primarily n-pentane and isopentane collectively and a second feed stream comprising primarily n-pentane and isopentane collectively. The method may further include subjecting the first feed stream to a first concentrating process, where the first concentrating process comprises distilling and produces a first product stream comprising primarily n-pentane and a second product stream that may comprise methane, ethane, and propane. The method may also include subjecting the second feed stream to a second concentrating process, where the second concentrating process comprises simulated moving bed adsorbing to produce a third product stream comprising primarily n-pentane and a fourth product stream comprising primarily isopentane.

Embodiments of the invention include a method of increasing n-pentane concentration in debutanized natural gasoline. The method may include splitting a stream that comprises primarily n-pentane and isopentane collectively, into a first feed stream comprising primarily n-pentane and isopentane collectively and a second feed stream comprising primarily n-pentane and isopentane collectively. The method may further include subjecting the first feed stream to a first concentrating process, where the first concentrating process comprises distilling and produces a first product stream comprising primarily n-pentane and a second product stream that may comprise methane, ethane, and propane. The first concentrating process may include distilling a combined stream that comprises a mixture of the first feed stream and a recycle stream having primarily isopentane to produce a bottoms stream comprising primarily n-hexane, an intermediate stream comprising primarily n-pentane, and an overhead stream comprising primarily isopentane. The first concentrating process may further comprise combining the intermediate stream and the bottoms stream to produce the first product stream, isomerizing the overhead stream in a reactor to convert at least some of the overhead stream's isopentane to n-pentane, and distilling effluent from the reactor to form the recycle stream and the second product stream. The method may further include subjecting the second feed stream to a second concentrating process, where the second concentrating process comprises simulated moving bed adsorbing to produce a third product stream comprising primarily n-pentane and a fourth product stream comprising primarily isopentane. The second concentrating process may include feeding the second feed stream at a first port in a series of adsorbent columns, feeding an eluent at a second port in the series of adsorbent columns, removing raffinate from a third port in the series of adsorbent columns, removing extract from a fourth port in the series of adsorbent columns, and simulating switching location of the first port, second port, third port, and fourth port repeatedly amongst each other.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

In the context of the present invention at least the following twenty embodiments are now described. Embodiment 1 is a method of increasing n-pentane concentration in debutanized natural gasoline. The method includes the steps of splitting a stream, comprising primarily n-pentane and isopentane collectively, into a first feed stream comprising primarily n-pentane and isopentane collectively and a second feed stream comprising primarily n-pentane and isopentane collectively; subjecting the first feed stream to a first concentrating process, the first concentrating process includes distilling and produces a first product stream comprising primarily n-pentane and a second product stream comprising methane, ethane, and propane; and subjecting the second feed stream to a second concentrating process, the second concentrating process includes simulated moving bed adsorbing to produce a third product stream comprising primarily n-pentane and a fourth product stream comprising primarily isopentane. Embodiment 2 is the method of embodiment 1, wherein the first concentrating process includes the steps of distilling a combined stream that contains a mixture of the first feed stream and a recycle stream having primarily isopentane to produce a bottoms stream comprising primarily n-hexane, an intermediate stream comprising primarily n-pentane, and an overhead stream comprising primarily isopentane; combining the intermediate stream and the bottoms stream to produce the first product stream; isomerizing the overhead stream in a reactor to convert at least some of the overhead stream's isopentane to n-pentane; and distilling effluent from the reactor to form the recycle stream and the second product stream. Embodiment 3 is the method of embodiment 2, wherein the isomerizing includes the steps of mixing the overhead stream with hydrogen to form a mixture and contacting the mixture with a catalyst under reaction conditions to isomerize at least some of the isopentane to n-pentane. Embodiment 4 is the method of embodiment 3, wherein the catalyst does not include zeolite and is selected from the group consisting of sulfated zirconia, platinum on alumina, platinum on alumina dosed with perchloroethylene or other chlorinating agent, flouridized catalyst, and combinations thereof. Embodiment 5 is the method of any of embodiments 3 and 4, wherein the reaction conditions include a reaction temperature of 130 to 276° C., a pressure of 15 to 30 bar and GHSV of 4 to 5.5. Embodiment 6 is the method of any of embodiments 2 to 5, wherein the effluent from the reactor contains 58 mol. % to 68 mol. % isopentane and 15 mol. % to 25 mol. % n-pentane. Embodiment 7 is the method of any of embodiments 2 to 6, wherein the recycle stream contains 62 mol. % to 72 mol. % isopentane and 15 mol. % to 25 mol. % n-pentane. Embodiment 8 is the method of any of embodiments 1 to 7, wherein the n-pentane/isopentane mol. ratio in the first feed stream and/or the second feed stream is in a range 1.20 to 1.40 and wherein the first product stream contains 85 mol. % to 95 mol. % n-pentane. Embodiment 9 is the method of any of embodiments 1 to 8, wherein the first feed stream and/or the second feed stream contains 45 mol. % to 55 mol. % n-pentane and 35 mol. % to 45 mol. % isopentane and wherein the first product stream contains 85 mol. % to 95 mol. % n-pentane. Embodiment 10 is the method of any of embodiments 1 to 9, wherein the first feed stream and/or the second feed stream contains 85 mol. % to 95 mol. % n-pentane and isopentane collectively. Embodiment 11 is the method of any of embodiments 1 to 10, wherein the first feed stream and/or the second feed stream further contains cypentane, cis pentene, and n-hexane. Embodiment 12 is the method of any of embodiments 1 to 11, wherein the second product stream further contains n-butane and isobutane. Embodiment 13 is the method of any of embodiments 1 to 12, wherein the overhead stream contains 82 mol. % to 92 mol. % isopentane and 6 mol. % to 16 mol. % neopentane. Embodiment 14 is the method of any of embodiments 1 to 13, wherein the intermediate stream contains 96 mol. % to 100 mol. % n-pentane. Embodiment 15 is the method of any of embodiments 1 to 14, wherein the bottoms stream contains 55 mol. % to 65 mol. % n-hexane and 35 mol. % to 45 mol. % cypentane. Embodiment 16 is the method of any of embodiments 1 to 15, wherein the second concentrating process includes the steps of feeding the second feed stream at a first port in a series of adsorbent columns; feeding an eluent at a second port in the series of adsorbent columns; removing raffinate from a third port in the series of adsorbent columns; removing extract from a fourth port in the series of adsorbent columns; and simulating switching location of the first port, second port, third port, and fourth port repeatedly amongst each other. Embodiment 17 is the method of embodiment 16, wherein the third product stream contains 70 to 95 mol. % n-pentane. Embodiment 18 is the method of any of embodiments 16 and 17, wherein the ports are configured in the following order consistent with the direction of liquid flow through the columns: eluent port, extract port, feed port, and raffinate port. Embodiment 19 is the method of any of embodiments 16 to 18, wherein the eluent contains at least one selection from the group consisting of: n-butane, isobutane and an alkane of different molecular weight than streams being separated. Embodiment 20 is the method of any of embodiments 16 to 19, wherein the raffinate contains the third product stream and the extract contains isopentane.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which:

FIG. 4 shows a method for increasing n-pentane concentration in debutanized natural gasoline, according to embodiments of the invention;

DETAILED DESCRIPTION OF THE INVENTION

Figure 2:
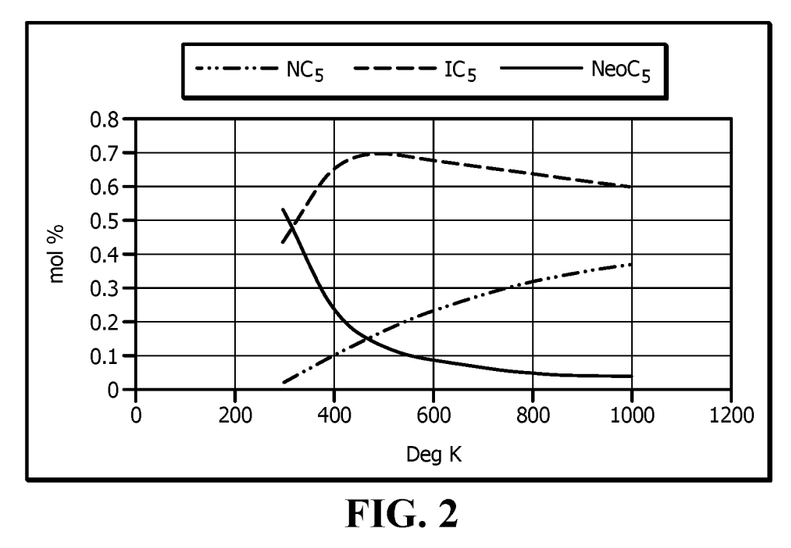
FIG. 2 shows equilibrium data for pentane isomers.

FIG. 2 shows equilibrium data for pentane isomers. As can be seen from FIG. 2, higher temperature favors n-pentane formation over isopentane formation. Thus, for an isomer separation column used to purify a particular throughput of a mixture of n-pentane/pentane isomers, as temperature increases, the size of the isomer separation column required decreases. However, as temperature increases, hydrocracking and formation of light ends increases. Thus, arriving at the ideal operating temperature involves counter balancing these two effects. Some research suggests that the ideal temperature to separate n-pentane and isopentane is about 276° C.

Some commercially available processes utilize shape selectivity of zeolites to increase branched hydrocarbon content as opposed to linear hydrocarbon content. However, for processes in which hydrocarbons are to be cracked, a high linear hydrocarbon/branched hydrocarbon ratio is preferred. Thus, the use of zeolite as a catalyst is undesirable for producing feedstock for these cracking processes.

A method has been discovered that increases the ratio of linear pentane/branched pentane in debutanized natural gasoline. By increasing this ratio, the utilization efficiency of debutanized natural gasoline as feedstock to thermal cracking units can be improved.

Figure 3:
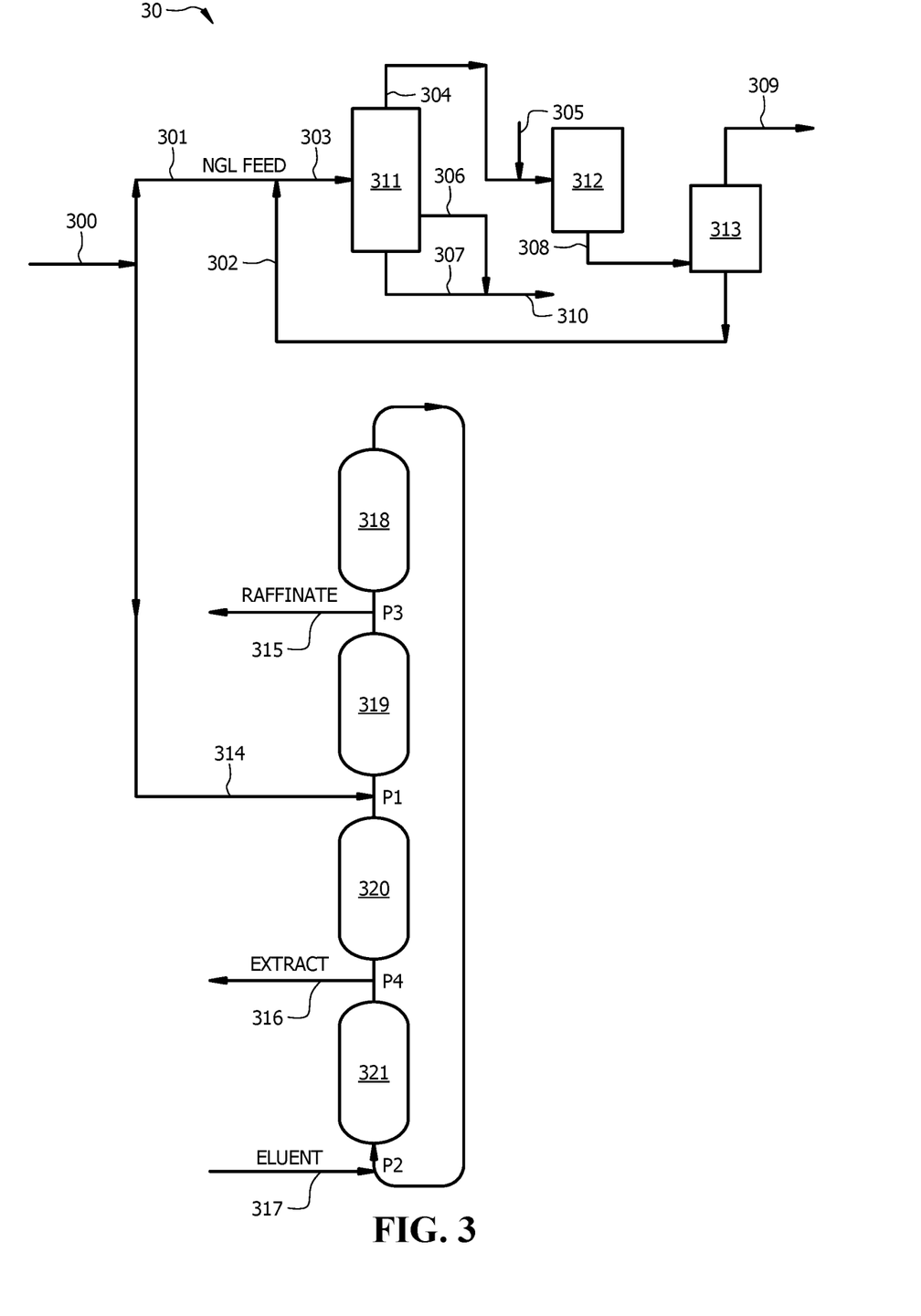
FIG. 3 shows a system for increasing n-pentane concentration in debutanized natural gasoline, according to embodiments of the invention.

FIG. 3 shows system 30 for increasing n-pentane concentration in debutanized natural gasoline, according to embodiments of the invention. FIG. 4 shows method 40 for increasing n-pentane concentration in debutanized natural gasoline, according to embodiments of the invention. Method 40 may be implemented using system 30.

Method 40 as implemented by system 30 may begin at block 400, which involves splitting feedstock 300 into first feed stream 301 and second feed stream 314. In embodiments of the invention, feedstock 300, and consequently first feed stream 301 and second feed stream 314, each may include primarily n-pentane and isopentane collectively. In embodiments of the invention, feedstock 300, first feed stream 301, and second feed stream 314 may each further include n-butane, cypentane, cis pentene, and n-hexane. First feed stream 301 and/or second feed stream 314 may each comprise 85 mol. % to 95 mol. % n-pentane and isopentane collectively. In embodiments of the invention, feedstock 300, first feed stream 301, and second feed stream 314 may each comprise 45 mol. % to 55 mol. % n-pentane and 35 mol. % to 45 mol. % isopentane. In embodiments of the invention, the n-pentane/isopentane mol. ratio in each of feedstock 300, first feed stream 301, and second feed stream 314 is in a range 1.20 to 1.40.

According to embodiments of the invention, at block 401, first feed stream 301 is subjected to a concentrating process, the concentrating process may include distilling and produces first product stream 310, which includes primarily n-pentane and second product stream 309, which may include methane, ethane, propane, isobutane, and n-butane.

At block 402, in embodiments of the invention, second feed stream 314 is also subjected to a concentrating process. Here, however, according to embodiments of the invention, subjecting second feed stream 314 to a concentrating separation process includes simulated moving bed adsorbing to produce third product stream 315, which may include primarily n-pentane and fourth product stream 316, which includes primarily isopentane.

Block 401 may include blocks 401-1 to 401-4. In embodiments of the invention, the concentrating process of block 401 includes, at block 401-1, distilling combined stream 303, which is a combination of first feed stream 301 and recycle stream 302 (comprising primarily isopentane), in distillation unit 311, to produce bottoms stream 307 (comprising primarily n-hexane), intermediate stream 306 (comprising primarily n-pentane), and overhead stream 304 (comprising primarily isopentane). In embodiments of the invention, overhead stream 304 comprises 82 mol. % to 92 mol. % isopentane and 6 mol. % to 16 mol. % neopentane; intermediate stream 306 comprises 96 mol. % to 100 mol. % n-pentane; and bottoms stream 307 comprises 55 mol. % to 65 mol. % n-hexane and 35 mol. % to 45 mol. % cypentane.

In embodiments of the invention, at block 401-2, intermediate stream 306 is combined with bottoms stream 307 to produce first product stream 310. In embodiments of the invention, first product stream 310 comprises 85 mol. % to 95 mol. % n-pentane. In embodiments of the invention, the composition of stream 310 is about 93 mol. % n-pentane, about 3 mol. % cyclopentane and about 4 mol. % n-hexane. First product stream 310 may also include n-hexane, cypentane, n-butane, isobutane, methane, ethane, and propane.

Method 40 may further include, at block 401-3, isomerizing overhead stream 304, in reactor 312, to convert at least some of overhead stream 304's isopentane to n-pentane. In embodiments of the invention, the isomerizing includes mixing overhead stream 304 with hydrogen 305 and contacting this mixture with a catalyst under reaction conditions sufficient to isomerize at least some of the isopentane to n-pentane. According to embodiments of the invention, the catalyst used in isomerizing the isopentane may include a selection from the list consisting of: sulfated zirconia, platinum on alumina, platinum on alumina dosed with perchloroethylene or other chlorinating agent, flouridized catalyst, and combinations thereof. However, in embodiments of the invention, the catalyst used does not contain zeolite because zeolite favors formation of branched hydrocarbons. The reaction conditions for the isomerization process in reactor 312 may include a reaction temperature of 130 to 276° C., a pressure of 15 to 30 bar and GHSV of 4 to 5.5. In embodiments of the invention, effluent 308 from reactor 312 comprises 58 mol. % to 68 mol. % isopentane and 15 mol. % to 25 mol. % n-pentane.

Method 40 may also include, at block 401-4, distilling effluent 308 from reactor 312, in distillation column 313, to form recycle stream 302 and second product stream 309. According to embodiments of the invention, recycle stream 302 may comprise 62 mol. % to 72 mol. % isopentane and 15 mol. % to 25 mol. % n-pentane. According to embodiments of the invention, second product stream 309 may comprise 20 mol. % to 30 mol. % methane, 20 mol. % to 30 mol. % ethane, 20 mol. % to 30 mol. % propane, 10 mol. % to 20 mol. % n-butane, and 5 mol. % to 15 mol. % isobutane.

In embodiments of the invention, a supplemental process for separating n-pentane from isopentane is provided. For example, in embodiments of the invention, the concentrating process of block 402 is provided. Block 402 may include a concentrating process using a simulated moving bed (SMB) of a typical adsorbent molecular sieve such as type 5A. Embodiments of the invention may utilize further enhanced capacity molecular sieves. Typical SMB operation involves moving eluant, extract, feed, and raffinate ports in a timed sequence. This movement of ports simulates movement of the solid bed without actually moving the solid bed. A programmable logic controller or a digital sequencer operates a number of solenoid valves that redirect the flows in a predetermined sequence. A digital sequencer has the advantage of having no moving parts. It is therefore more reliable than any other technique to implement a simulated moving bed.

Block 402 may include blocks 402-1 to 402-4. Block 402-1 may include feeding second feed stream 314 at first port P1 in a series of adsorbent columns 318 to 321. In embodiments of the invention, block 402-2 involves feeding eluent 317 at second port P2 in the series of adsorbent columns 318 to 321. The eluent may include n-butane or isobutane, an alkane of different molecular weight than the streams being isomerized. At block 402-3, raffinate is removed from third port P3 in the series of adsorbent columns 318 to 321. In embodiments of the invention, method 40 further includes, removing extract from a fourth port in the series of adsorbent columns 318 to 321. According to embodiments of the invention, the raffinate comprises third product stream 315 and the extract comprises fourth product stream 316. In embodiments of the invention, third product stream 315 comprises 70 to 95 mol. % n-pentante and fourth product stream 316 comprises 80 to 95 mol. % isopentante.

According to embodiments of the invention, block 402-4 involves simulating location switching of first port P1, second port P2, third port P3, and fourth port P4 repeatedly amongst each other, while maintaining the following order consistent with the direction of liquid flow through the columns: eluent port, extract port, feed port, and raffinate port.

Figure 5:
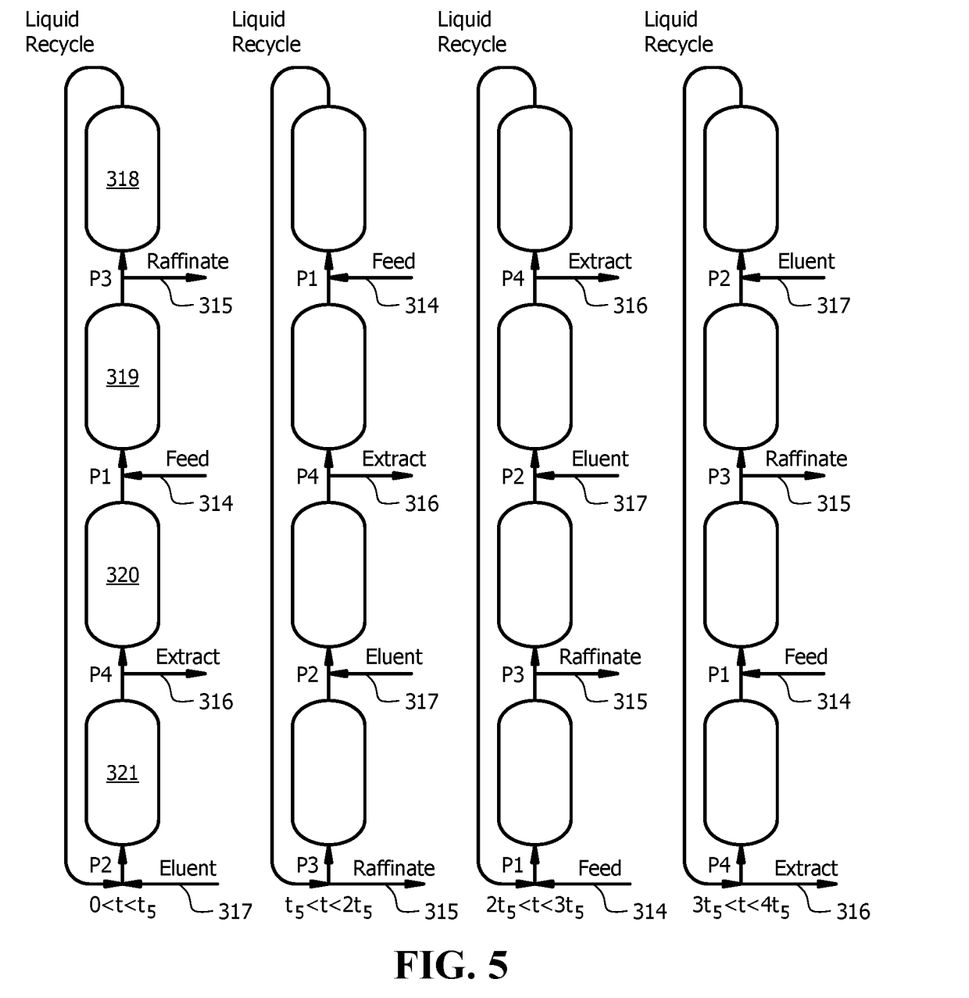
FIG. 5 shows different sequences of a series of simulated bed adsorbent columns, according to embodiments of the invention.

FIG. 5 shows different sequences of the series of simulated bed adsorbent columns 318 to 321, according to embodiments of the invention. The different sequences are a result of the simulated switching and show ports P1 to P4 are located in different positions consistent with the simulated moving bed.

Although embodiments of the present invention have been described with reference to blocks of FIG. 4, it should be appreciated that operation of the present invention is not limited to the particular blocks and/or the particular order of the blocks illustrated in FIG. 40. For example, embodiments of the invention may include the concentration process described in block 401, without the concentration process described in block 402. Likewise, embodiments of the invention may include the concentration process described in block 402, without the concentration process described in block 401. Further, embodiments of the invention may provide functionality as described herein using various blocks in a sequence different than that of FIG. 4.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLES

Example 1

Material Balance of the First Concentration Process

Table 1 below shows a simulated material balance for the first concentration process as described with respect to block 401 above.

TABLE 1

| | | | | | DIP Colum | | | | | |
|---|---|---|---|---|---|---|---|---|---|---|
| | H2 | NGL Feed | Feed + Rec | Ovhd | Side draw | Bottom | Rx exit | Scrub ovhd | Recycle | nPentane |
| | | | | | Stream # | | | | | |
| | 305 mol % | 301 mol % | 303 mol % | 304 mol % | 306 mol % | 307 mol % | 308 mol % | 309 mol % | 302 mol % | 309 + 310 wt % |
| $H_2$ | 100.00% | | | | | | | | | 0.00% |
| $CH_4$ | | | | | | | 1.30% | 24.75% | | 0.53% |
| $C_2H_6$ | | | | | | | 1.33% | 25.31% | | 1.02% |
| $C_3H_8$ | | | | | | | 1.33% | 25.31% | | 1.50% |
| isobutane | | | | | | | 0.50% | 9.53% | | 0.74% |
| nButane | | 0.08% | 0.03% | 0.04% | 0.00% | 0.00% | 0.79% | 15.11% | | 1.18% |
| Isopentane | | 40.91% | 57.70% | 88.09% | 0.00% | 0.00% | 63.69% | 0.00% | 67.21% | 0.00% |
| nPentane | | 50.18% | 32.19% | 0.00% | 100.00% | 0.00% | 19.53% | 0.00% | 20.61% | 88.07% |
| neopentane | | | 7.78% | 11.87% | 0.00% | 0.00% | 11.54% | 0.00% | 12.18% | 0.00% |
| CyPentane | | 2.48% | 0.90% | 0.00% | 0.00% | 38.99% | 0.00% | 0.00% | 0.00% | 2.38% |

TABLE 1-continued

| | | DIP Colum | | | | | | | | |
|---|---|---|---|---|---|---|---|---|---|---|
| | H2 | NGL Feed | Feed + Rec | Ovhd | Side draw | Bottom | Rx exit | Scrub ovhd | Recycle | nPentane |
| | | | | | Stream # | | | | | |
| | 305 mol % | 301 mol % | 303 mol % | 304 mol % | 306 mol % | 307 mol % | 308 mol % | 309 mol % | 302 mol % | 309 + 310 wt % |
| Cis2Pentene | | 2.48% | 0.00% | 0.00% | 0.00% | 0.00% | 0.00% | 0.00% | 0.00% | 0.00% |
| nHexane | | 3.88% | 1.40% | 0.00% | 0.00% | 61.01% | 0.00% | 0.00% | 0.00% | 4.58% |
| Total | | 100.01% | 100.00% | 100.00% | 100.00% | 100.00% | 100.00% | 100.00% | 100.00% | 100.00% |
| MW Kg/Kgmol | | 72.58 | 72.32 | 72.14 | 72.15 | 79.92 | 70.31 | 37.06 | 72.15 | 69.36 |
| t/hr | 0.45 | 184.00 | 507.19 | 331.42 | 162.88 | 12.88 | 332.24 | 9.19 | 323.06 | 184.95 |
| Mass Balance Error t/h | | −0.49 | | | | | | | | |

Example 2

Distillation Column

Figure 6:
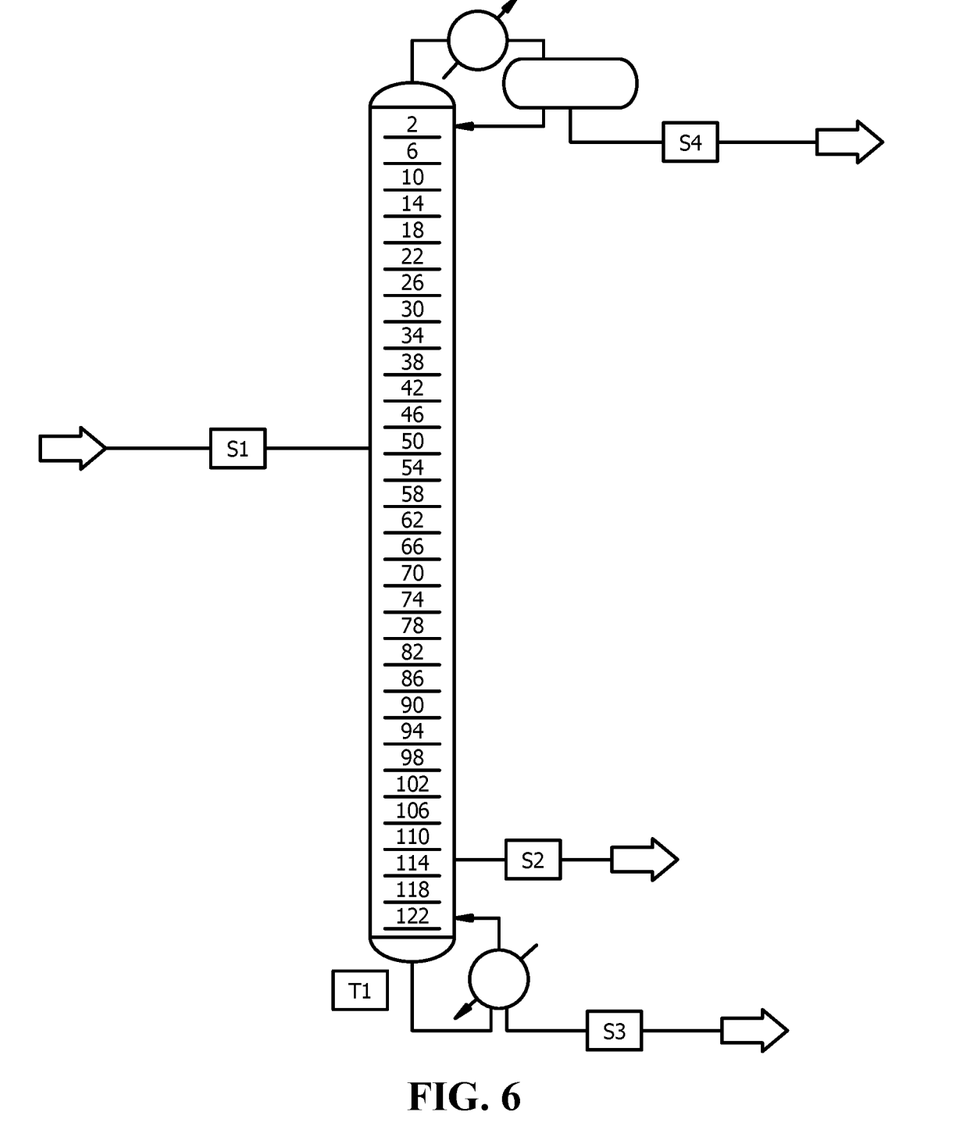
FIG. 6 shows a distillation column for performing the separation of n-pentane and isopentane, according to embodiments of the invention.

FIG. 6 shows distillation column 60 for performing the separation of n-pentane and isopentane, according to embodiments of the invention. Distillation column 60 may be used to function as distillation unit 311 in system 30 to carry out the distillation described in block 401-1 of method 40. Table 2 below shows a simulation of the separation duty for distillation column 60 in implementing the distillation described in block 401-1 of method 40.

TABLE 2

| | | Stream Name | | | |
|---|---|---|---|---|---|
| Stream Description | | S1 | S2 | S3 | S4 |
| Phase | | Liquid | Liquid | Liquid | Liquid |
| Temperature | C. | 45.000 | 82.573 | 83.829 | 70.661 |
| Pressure | KG/CM2 | 4.100 | 4.022 | 4.024 | 4.000 |
| Total Mass Rate | KG/NR | 507119.000 | 0.000 | 175468.284 | 331650.716 |
| Total Weight Comp. Percent | | | | | |
| $H_2$ | | 0.0000 | 0.0000 | 0.0000 | 0.0000 |
| METHANE | | 0.0000 | 0.0000 | 0.0000 | 0.0000 |
| ETHANE | | 0.0000 | 0.0000 | 0.0000 | 0.0000 |
| PROPANE | | 0.0000 | 0.0000 | 0.0000 | 0.0000 |
| ISOBUTANE | | 0.0000 | 0.0000 | 0.0000 | 0.0000 |
| BUTANE | | 0.0241 | 0.0000 | 0.0000 | 0.0369 |
| NEOPENTANE | | 7.7613 | 0.0000 | 0.0000 | 11.8675 |
| IPENTANE | | 57.5612 | 0.0000 | 0.0014 | 88.0146 |
| PENTANE | | 32.1125 | 99.2818 | 92.6552 | 0.0809 |
| CP | | 0.8727 | 0.4542 | 2.5223 | 0.0000 |
| HEXANE | | 1.6682 | 0.2557 | 4.8211 | 0.0000 |

Example 3

Design of Simulated Moving Bed

Table 3 shows an example of a typical design for a simulated moving bed, which may be used to implement the concentrating described above in block 402.

TABLE 3

| nPentaniser Separation Design using SMB | | Typical design |
|---|---|---|
| Number of columns | | 60.00 |
| Column length | meter | 2.21 |
| Column diameter | meter | 9.50 |
| Adsorbent volume | $m^3$ | 9381.97 |
| particle size | $m10^{-3}$ meter | 0.30 |
| aspect ratio | D/L | 4.31 |
| productivity | kg/(hr $m^3$ adsorbent) | 54.00 |
| adsorbent capacity | kg/$m^3$ adsorbent | 90.00 |
| Adsorbed adsorbate in all beds at a time | | 844376.93 |
| switches per minute | | 3.63 |
| Switches per hr | | 218.00 |

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of increasing n-pentane concentration in debutanized natural gasoline, the method comprising:
   splitting a stream, comprising primarily n-pentane and isopentane collectively, into a first feed stream comprising primarily n-pentane and isopentane collectively and a second feed stream comprising primarily n-pentane and isopentane collectively;
   subjecting the first feed stream to a first concentrating process, the first concentrating process comprises distilling and produces a first product stream comprising primarily n-pentane and a second product stream comprising methane, ethane, and propane; and
   subjecting the second feed stream to a second concentrating process, the second concentrating process comprises simulated moving bed adsorbing to produce a third product stream comprising primarily n-pentane and a fourth product stream comprising primarily isopentane;
   wherein the first feed stream and/or the second feed stream comprises 85 mol. % to 95 mol. % n-pentane and isopentane collectively.

2. The method of claim 1, wherein the first concentrating process comprises:
   distilling a combined stream that comprises a mixture of the first feed stream and a recycle stream having primarily isopentane to produce a bottoms stream comprising primarily n-hexane, an intermediate stream comprising primarily n-pentane, and an overhead stream comprising primarily isopentane;
   combining the intermediate stream and the bottoms stream to produce the first product stream;
   isomerizing the overhead stream in a reactor to convert at least some of the overhead stream's isopentane to n-pentane; and
   distilling effluent from the reactor to form the recycle stream and the second product stream.

3. The method of claim 2, wherein the isomerizing includes mixing the overhead stream with hydrogen to form a mixture and contacting the mixture with a catalyst under reaction conditions to isomerize at least some of the isopentane to n-pentane.

4. The method of claim 3, wherein the catalyst does not include zeolite and is a selection from the list consisting of: sulfated zirconia, platinum on alumina, platinum on alumina dosed with perchloroethylene or other chlorinating agent, flouridized catalyst, and combinations thereof.

5. The method of claim 3, wherein the reaction conditions include a reaction temperature of 130 to 276° C., a pressure of 15 to 30 bar and GHSV of 4 to 5.5.

6. The method of claim 4, wherein the catalyst is platinum on alumina dosed with perchloroethylene.

7. The method of claim 4, wherein the catalyst is a flouridized catalyst.

8. The method of claim 1, wherein the catalyst does not contain a zeolite.

9. The method of claim 1, wherein the first feed stream and/or the second feed stream further comprises cypentane, cis pentene, and n-hexane.

10. The method of claim 1, wherein the second product stream further comprises n-butane and isobutane.

11. The method of claim 1, wherein the overhead stream comprises 82 mol. % to 92 mol. % isopentane and 6 mol. % to 16 mol. % neopentane.

12. The method of claim 1, wherein the intermediate stream comprises 96 mol. % to 100 mol. % n-pentane.

13. The method of claim 1, wherein the bottoms stream comprises 55 mol. % to 65 mol. % n-hexane and 35 mol. % to 45 mol. % cypentane.

14. A method of increasing n-pentane concentration in debutanized natural gasoline, the method comprising:
   splitting a stream, comprising primarily n-pentane and isopentane collectively, into a first feed stream comprising primarily n-pentane and isopentane collectively and a second feed stream comprising primarily n-pentane and isopentane collectively;
   subjecting the first feed stream to a first concentrating process, the first concentrating process comprises distilling and produces a first product stream comprising primarily n-pentane and a second product stream comprising methane, ethane, and propane; and
   subjecting the second feed stream to a second concentrating process, the second concentrating process comprises simulated moving bed adsorbing to produce a third product stream comprising primarily n-pentane and a fourth product stream comprising primarily isopentane, wherein the second concentrating process comprises:
   feeding the second feed stream at a first port in a series of adsorbent columns;
   feeding an eluent at a second port in the series of adsorbent columns;
   removing raffinate from a third port in the series of adsorbent columns; removing extract from a fourth port in the series of adsorbent columns; and
   simulating switching location of the first port, second port, third port, and fourth port repeatedly amongst each other.

15. The method of claim 14, wherein the third product stream comprises 70 to 95 mol. % n-pentane.

16. The method of claim 14, wherein the ports are configured in the following order consistent with the direction of liquid flow through the columns: eluent port, extract port, feed port, and raffinate port.

17. The method of claim 14, wherein the eluent comprises a selection from the list consisting of: n-butane, isobutane, an alkane of different molecular weight than streams being separated, and combinations thereof.

18. The method of claim 14, wherein the raffinate comprises the third product stream and the extract comprises isopentane.

19. The method of claim 2, wherein the effluent from the reactor comprises 58 mol. % to 69 mol. % isopentane and 15 mol. % to 25 mol. % n-pentane.

* * * * *